US009977925B2

(12) United States Patent
Riehle et al.

(10) Patent No.: US 9,977,925 B2
(45) Date of Patent: May 22, 2018

(54) DEVICE FOR DETERMINING AN AMOUNT OF INSULIN TO BE INJECTED FOR DIABETES PATIENTS

(71) Applicant: IWA-F. Riehle GmbH & Co KG, Denkendorf (DE)

(72) Inventors: Harald Riehle, Stuttgart (DE); Gerhard Grebing, Nuertingen (DE)

(73) Assignee: IWA—F. RIEHLE GmbH & Co KG, Denkendorf (DE)

( * ) Notice: Subject to any disclaimer, the term of this patent is extended or adjusted under 35 U.S.C. 154(b) by 12 days.

(21) Appl. No.: 15/111,186

(22) PCT Filed: Jul. 18, 2014

(86) PCT No.: PCT/EP2014/065555
§ 371 (c)(1),
(2) Date: Jul. 13, 2016

(87) PCT Pub. No.: WO2015/106839
PCT Pub. Date: Jul. 23, 2015

(65) Prior Publication Data
US 2016/0328581 A1    Nov. 10, 2016

(30) Foreign Application Priority Data

Jan. 17, 2014   (DE) .......................... 10 2014 200 866

(51) Int. Cl.
*G06G 1/02* (2006.01)
*G06G 1/00* (2006.01)
*G09B 19/02* (2006.01)

(52) U.S. Cl.
CPC ............. *G06G 1/001* (2013.01); *G09B 19/02* (2013.01)

(58) Field of Classification Search
CPC ............. G06G 1/00; G06G 1/045; G06G 1/06; G06G 1/08; G06G 3/00; G06G 3/08
(Continued)

(56) References Cited

U.S. PATENT DOCUMENTS 2,353,163 A    7/1944   Keinath
3,514,582 A    5/1970   Sanderson
(Continued)

FOREIGN PATENT DOCUMENTS

DE    27 21 302    11/1978
GB    2 189 633    10/1987
(Continued)

OTHER PUBLICATIONS

Wikipedia, "Slide rule", Jun. 16, 2014, 15:43.
IWA, "Dosimeter Insulin", http://www.archive.org, Nov. 13, 2008.

*Primary Examiner* — Daniel St Cyr
(74) *Attorney, Agent, or Firm* — Paul Vincent

(57) ABSTRACT

The invention relates to a slide device (1) for ascertaining an amount of insulin to be injected, comprising portions of flat material arranged in layers, which form a disk-like housing body (52), having a plurality of slide tongues displaceable counter to one another, wherein a first slide tongue (8) has a plurality of input scales (16), each with an equidistant line graduation, and a output scale (18), and can be manually grasped for the intended use and is displaceable in a first direction (14); wherein each input scale (16) is assigned a first parameter (37); wherein a second slide tongue (30) is displaceable in a second direction (32), which extends transversely to the first direction (14), and has a window (34) with a setting mark (35), which can be positioned relative to the housing body (52) in such a way that a visual inspection selectively of each of the input scales (16) is enabled; wherein next to the second slide tongue (30), a third slide tongue (38) is displaceable in the second direction (32) and
(Continued)

Figure 1C:
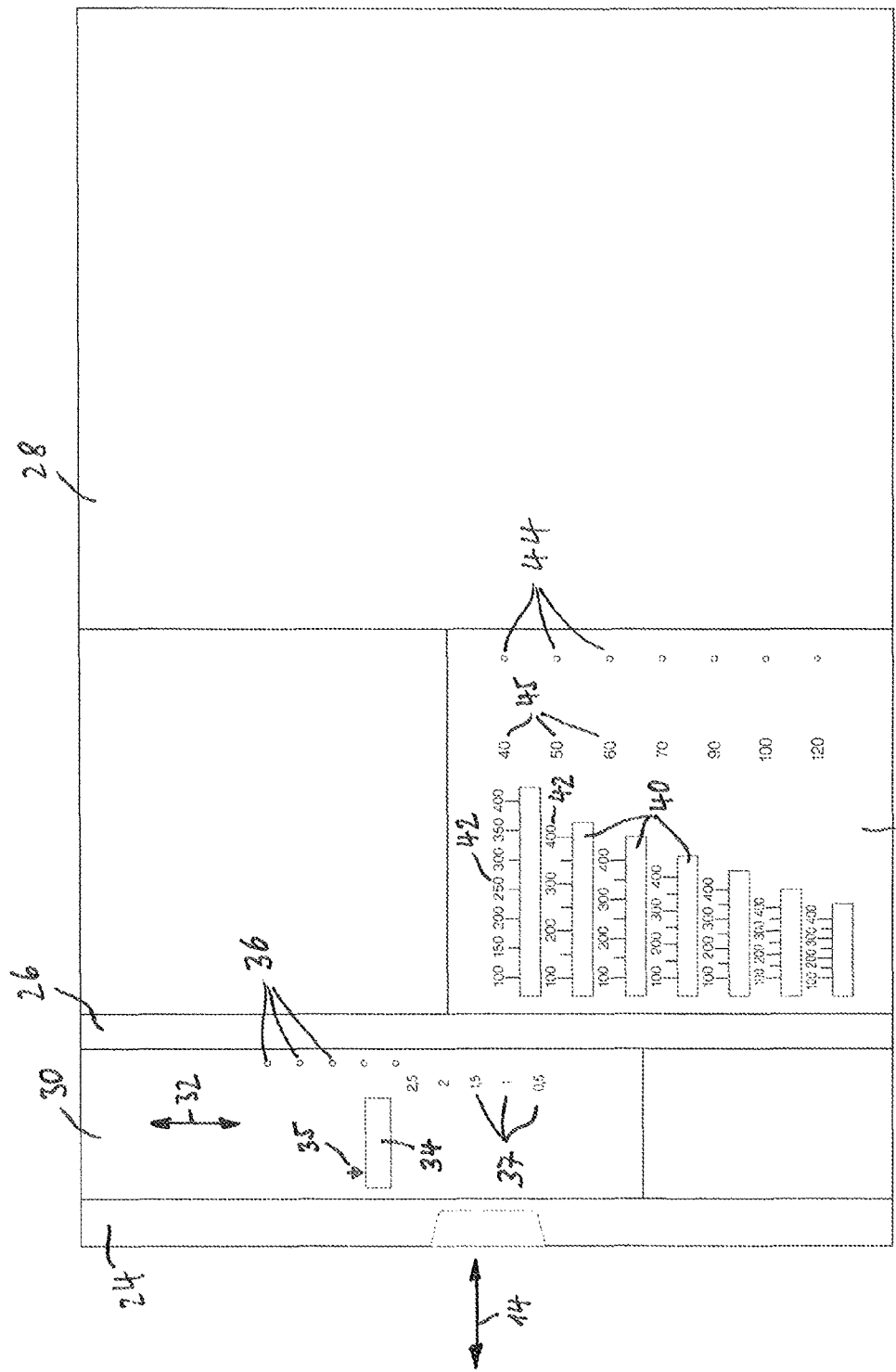

has a plurality of windows (40), which are embodied and arranged in such a way that each window (40), in a suitably selectable displacement position of the third slide tongue (38) relative to the housing body (52), enables a visual inspection of the output scale (18); and wherein each window (40) of the third slide tongue (38) on its periphery in the first direction has a reading scale (42) with an equidistant line graduation, and each reading scale (42) is assigned a second parameter (45); and wherein the second slide tongue (30) and the third slide tongue (38) can be placed nondisplaceably in a respective positioning relative to the housing body (52); and wherein after the second and third slide tongues (30, 38) have been positioned, the first slide tongue (8) can be positioned opposite the setting mark (35) at the window (34) of the second slide tongue (30) and then, at a value of the reading scale (42) as a reading mark, a value on the output scale (18) can be read out, which is equivalent to the amount of insulin to be injected.

14 Claims, 18 Drawing Sheets

(58) Field of Classification Search
USPC .................................. 235/66, 61 R, 83, 84
See application file for complete search history.

(56) References Cited

U.S. PATENT DOCUMENTS

| | | | |
|---|---|---|---|
| 4,313,054 A | 1/1982 | Martini | |
| 5,786,584 A * | 7/1998 | Button | A61B 5/14532 235/375 |
| 6,543,682 B1 * | 4/2003 | Glaser | G06C 3/00 235/66 |
| 6,779,480 B2 * | 8/2004 | Zamjahn | G09F 11/23 116/308 |
| 8,910,858 B2 * | 12/2014 | McDonald | A61J 7/04 235/61 R |

FOREIGN PATENT DOCUMENTS

| | | |
|---|---|---|
| WO | WO 2005/081173 | 9/2005 |
| WO | WO 2005/091208 | 9/2005 |
| WO | WO 2006/079124 | 7/2006 |

* cited by examiner

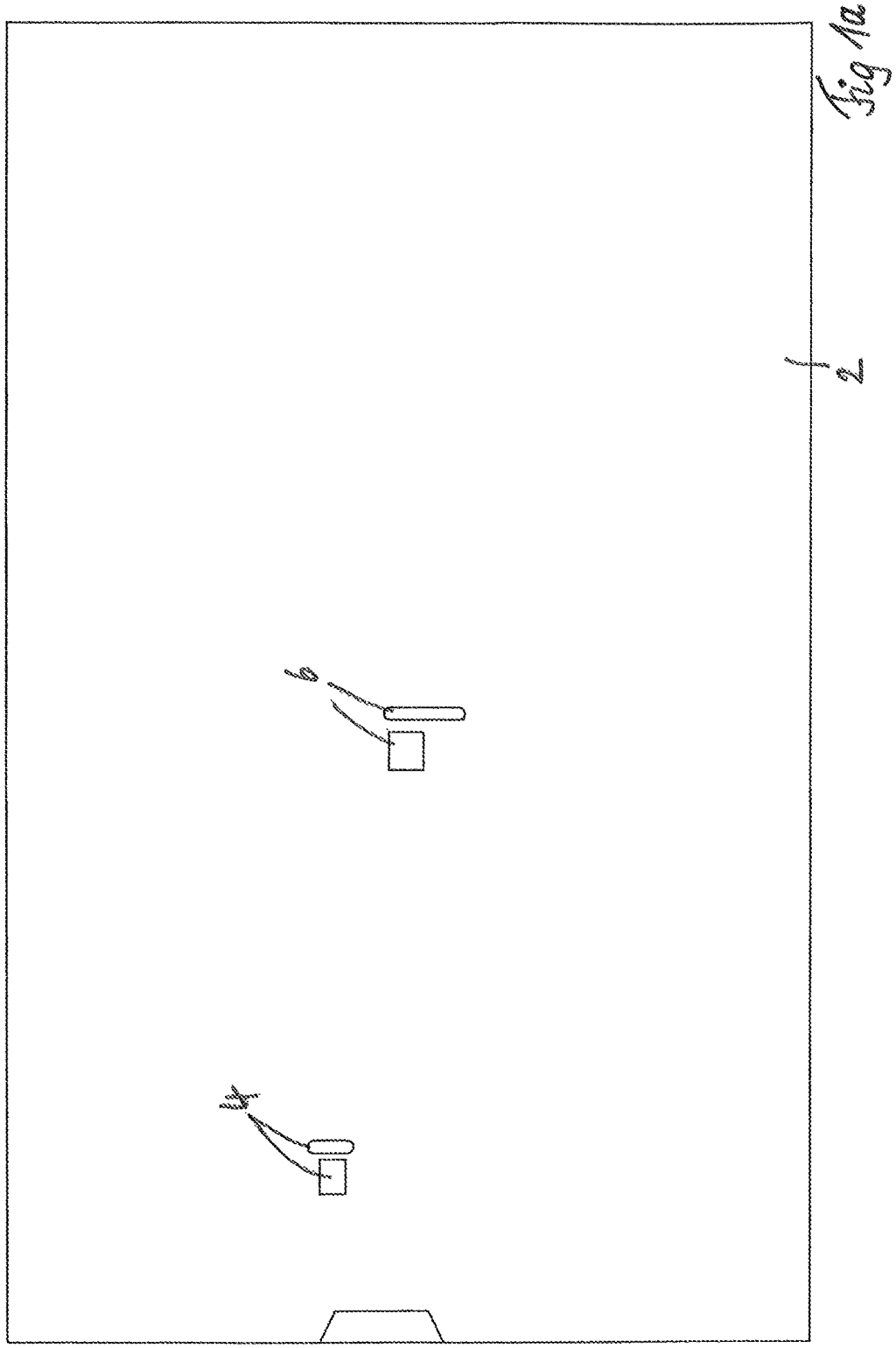

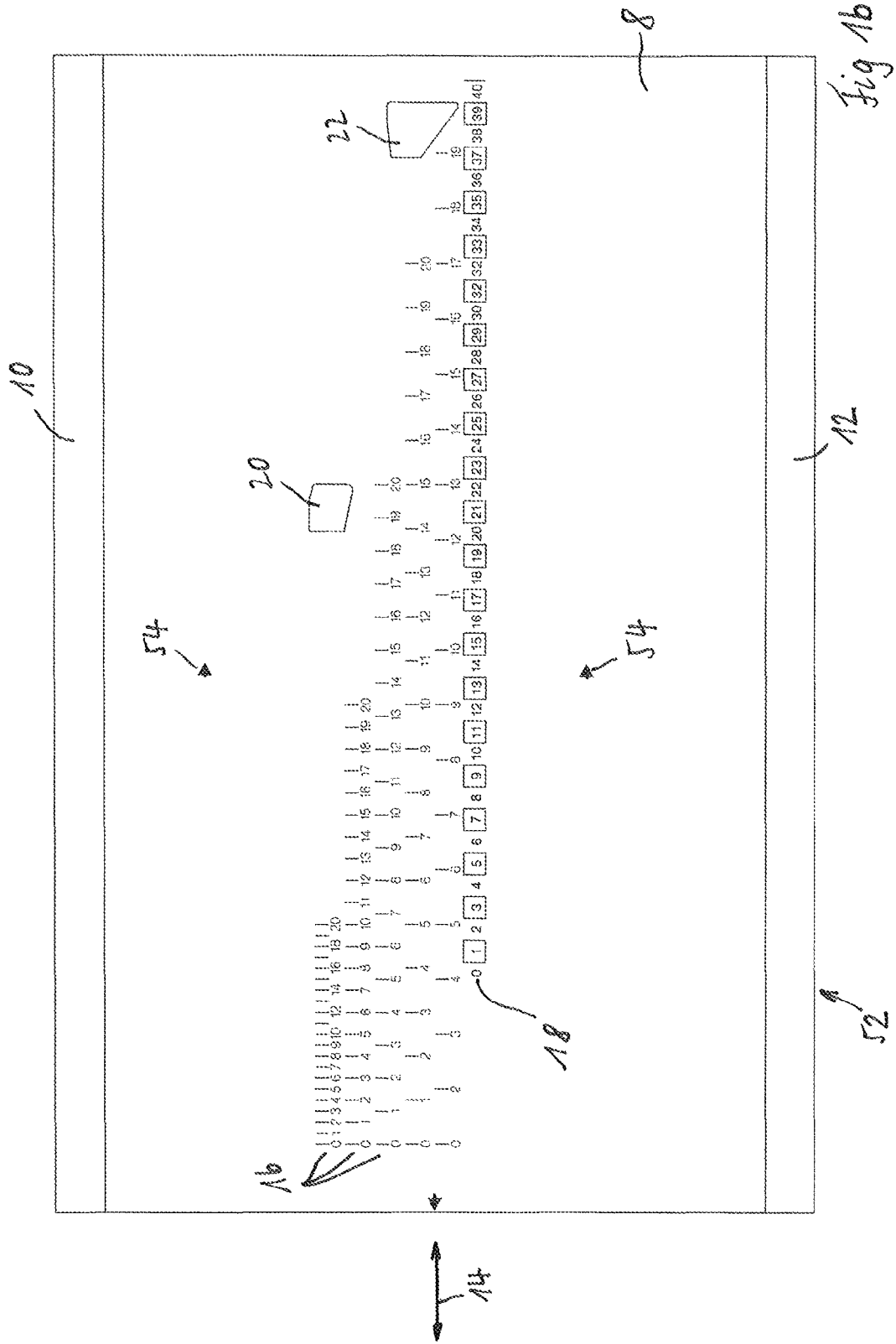

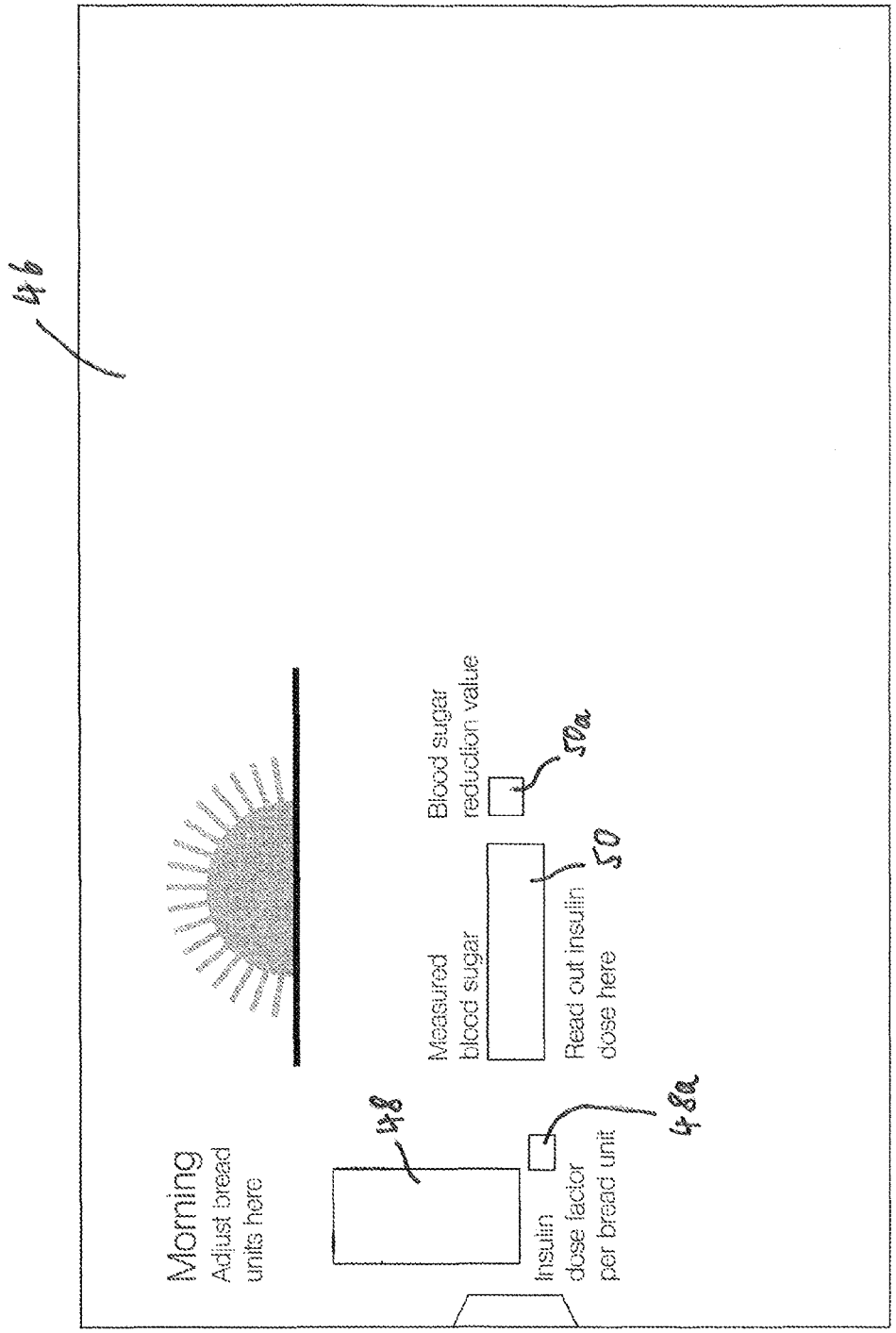

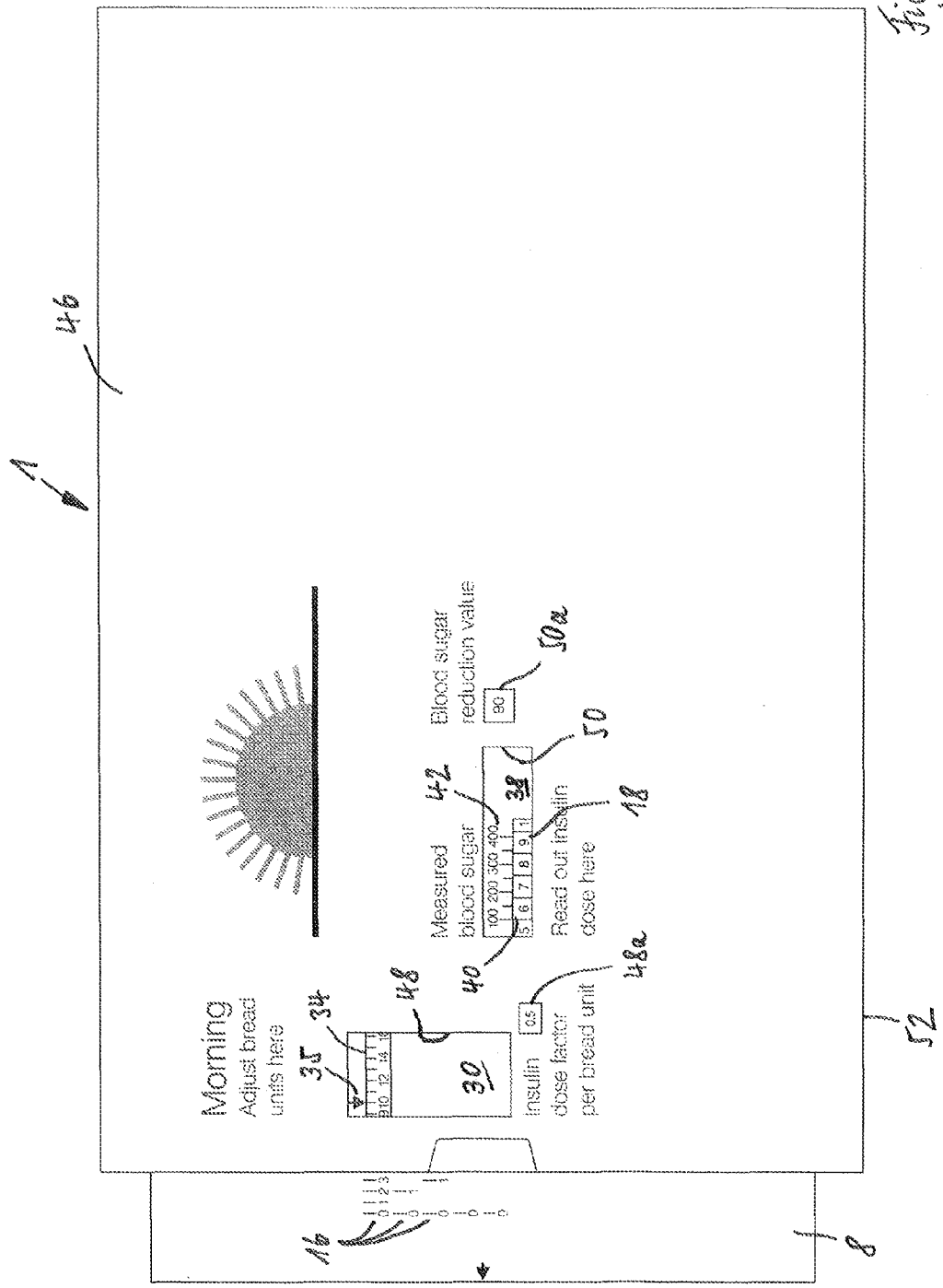

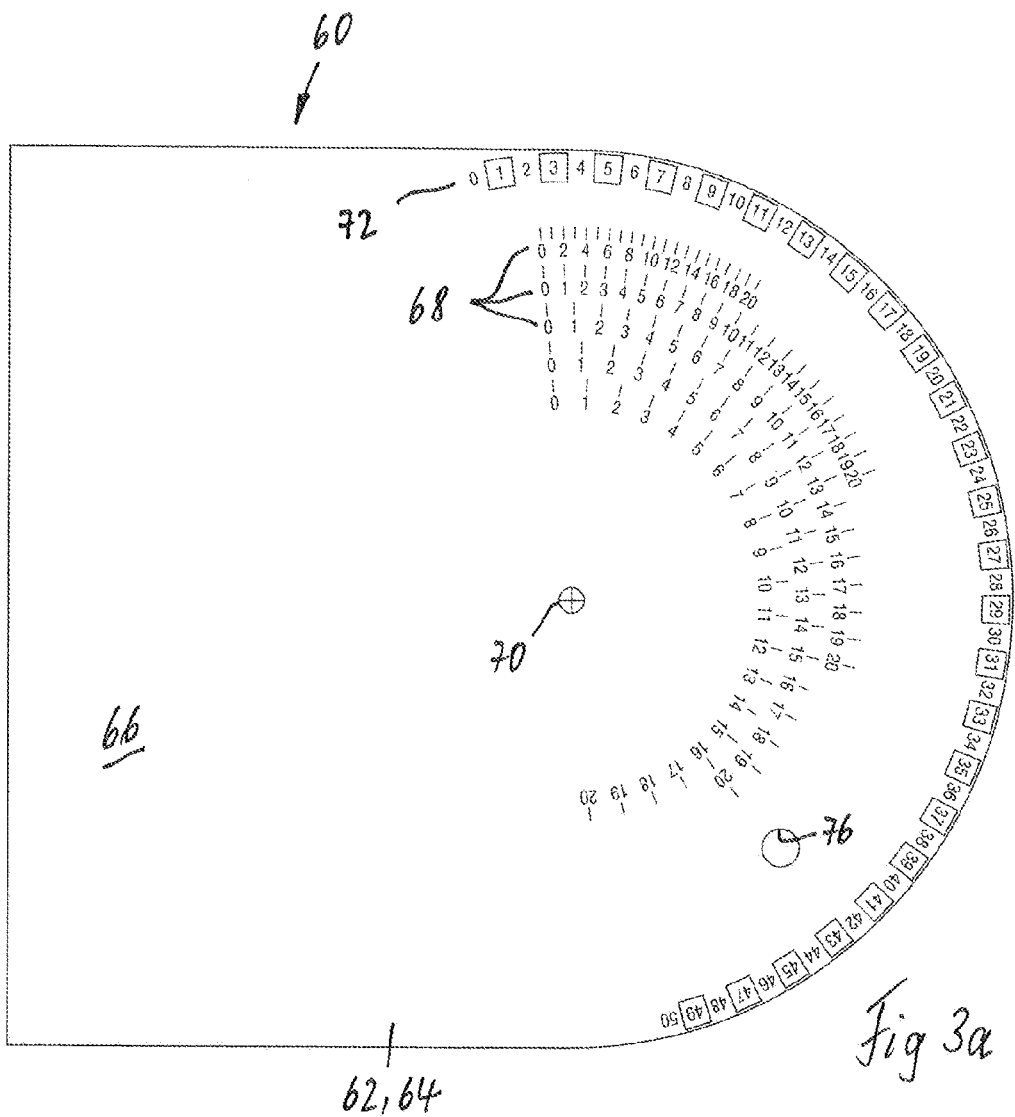

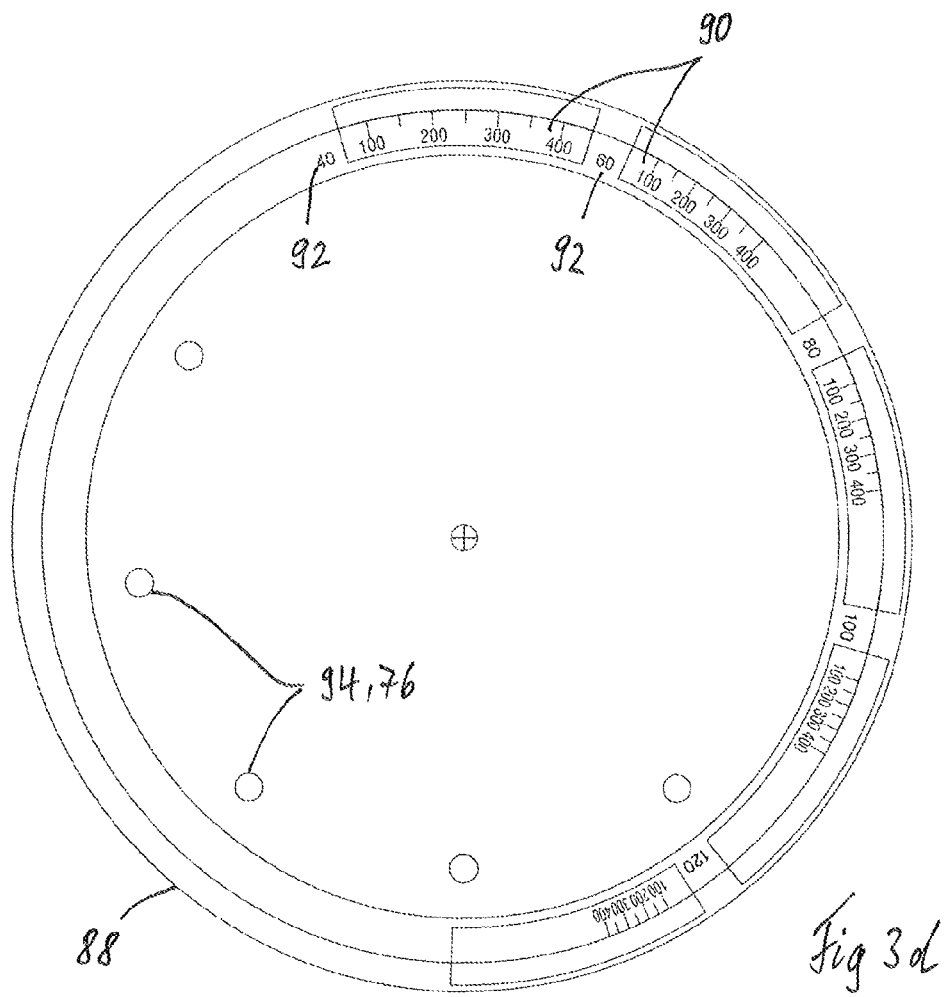

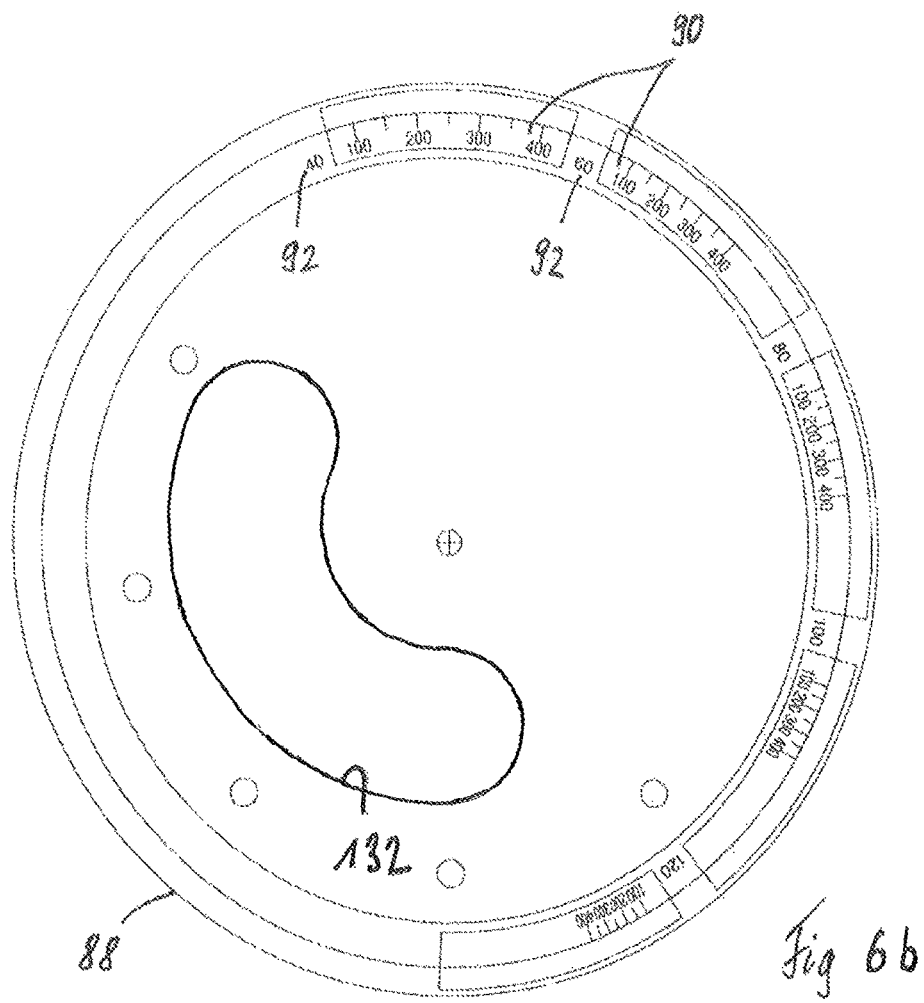

A: First, we calculate the amount of insulin for the meal

| Line 1. | How many bread units (BE) or carbohydrate exchange units (KE) do you want to eat now for this meal? | | | 3 |
|---|---|---|---|---|
| 2. | How many bread units (BE) or carbohydrate exchange units (KE) do you want to eat for a snack in one to two hours? | | | 0,5 |
| 3. | From the above, the total amount of bread units (BE) or carbohydrate exchange units (KE) is found. (calculate 1. + 2.) | | | 3,5 |
| 4. | Now look for the insulin factor for the time of day: | | | |
|  | Morning | Midday | Evening | Late |
| 5. | 0,75 | 0,5 | 0,5 | 0,5 |
| 6. | Now take the total amount of BE or KE with the insulin factor for the time of day times: | | | |
| 7. | Insulin factor is (select from 5.) | 0,5 | 3,5 | 1,75 |

B: Second, we calculate the amount of insulin for correcting the current blood sugar

| 8. | What was the blood sugar value you have just now measured? | | | 120 |
|---|---|---|---|---|
| 9. | Now look for your blood sugar target value for the time of day: | | | |
|  | Morning | Midday | Evening | Late |
| 10. | 100 | 100 | 120 | 120 |
| 11. | Subtract the target value from the measured blood sugar value: | | | |
| 12. | 120 | Blood sugar reduction value (select from 10.) | 100 | 20 |
| 13. | Now look for your blood sugar reduction value for the time of day: | | | |
|  | Morning | Midday | Evening | Late |
| 14. | 50 | 80 | 80 | 100 |
| 15. | Now divide the correction amount by the blood sugar reduction value. | | | |
| 16. | Correction amount (result from 12.) | 20 | 80 | 0,25 |

C: Combine the two results of calculation:

| 17. | How many units do you have to inject for the meal? (from 7.) | 1,75 |
|---|---|---|
| 18. | How many units do you have to inject for blood sugar correction? (from 16.) | 0,25 |
| 19. | All in all, an amount of insulin that is now to be injected is found: --->>> All of this is for the Insuman Rapid (red pen) | 2,0 |

Fig. 7

DEVICE FOR DETERMINING AN AMOUNT OF INSULIN TO BE INJECTED FOR DIABETES PATIENTS

The invention relates to a device for ascertaining an amount of insulin to be injected for diabetes patients.

Diabetes patients must inject amounts of insulin typically several times a day, in particular in the morning, at midday, in the evening and in late evening, in accordance with the number of bread units or carbohydrate exchange units to be eaten. The amount of insulin to be injected, that is, the number of insulin units to be injected, however, depends not only on the amount of bread units or carbohydrate exchange units eaten or to be eaten immediately, but also on parameters specific to the time of day, which moreover have to be ascertained patient-specifically. In this respect, the so-called insulin factor is identified, which is typical for the particular time of day, that is, morning, midday, evening and late evening, which is ascertained by the physician treating the patient or by a therapist for a patient and in a sense fixedly written, along with the blood sugar target value and the blood sugar reduction value, which are also ascertained patient-specifically for the particular time of day and made the basis for that patient. Moreover, ascertaining an amount of insulin to be injected always involves measuring the current blood sugar value. A deviation between the current blood sugar value and the aforementioned blood sugar target value is ascertained and linked with the aforementioned blood sugar reduction value in order from this to attain a correction value or correction amount of insulin which has to be injected in addition, regardless of the amount of bread units or carbohydrate exchange units to be eaten.

WO 2005/081173 A1 and WO 2006/079124 A2 disclose slide devices having a plurality of slide tongues displaceable relative to one another in a longitudinal direction and parallel, which are intended to serve as a function of parameters, such as the currently measured blood sugar, the nutrition taken or to be taken, for calculating an amount of insulin to be injected. In WO 2006/079124 A2, not only a slide device but also a dial device with three dials rotatable counter to one another is disclosed, which serves the same purpose. With DE 27 21 302 A1, the suggestion has already been made, in a dial device, of fixing two disks, rotatable counter to one another, removably relative to one another by means of an adhesive film placed between them. U.S. Pat. No. 3,514,582 shows a calculation slide with a longitudinally displaceable slide tongue and a reading mark that can be displaced transversely using one's thumb.

The object of the present invention is to furnish a simple device for ascertaining an amount of insulin to be injected that above all can be manipulated safely and that, especially for children suffering from diabetes type 1 and 2 but also for adults, is suitable for offering secure protection against mistakes in use.

This object is attained in a first variant of the invention by a slide device having the features of claim 1 and in a second variant of the invention by a dial device having the features of claim 12.

In the bread unit of the invention, the plurality of slide tongues or their various scales are positioned relative to one another such that a user, at a specific value of the reading scale as a reading mark, can immediately and directly read out the amount of insulin to be injected; this specific value of the reading scale corresponds to the current blood sugar value that has just been measured. The various input scales and their respective equidistant line graduation correspond to the input of the amount of bread units or carbohydrate exchange units to be eaten, on the basis of a specific parameter, in particular in the form of the aforementioned insulin factor for a given input scale. By positioning the second slide tongue with its window over a specific input scale, the first parameter that is to be made the basis for the calculation to be performed is defined. By positioning the third slide tongue in such a way that one of its windows enables visual inspection of the output scale of the first slide tongue, a specific reading scale corresponding to the second parameter is positioned at the output scale of the first slide tongue, and in this way the second parameter for the calculation to be made is defined. All that needs to be done now is to put the first slide tongue into a displacement position such that the setting mark on the window of the second slide tongue for the quantity of bread units or carbohydrate exchange units to be eaten is positioned on the input scale. After the current blood sugar value is measured, the amount of insulin to be injected can then be read off directly in the window of the third slide tongue on the output scale, and more specifically at the currently measured blood sugar value of the reading scale, which for this purpose in a sense forms a reading mark.

Since the first parameter and the second parameter are patient-specific and are prescribed for a given time of day by the physician or therapist, it would be appropriate for the diabetes patient to have available a separate device for each time of day, in which device the second and third slide tongues are already adjusted to a sliding position corresponding to the time of day. To this extent, it proves to be advantageous if a displacement of the second slide tongue or of the third slide tongue and preferably of both of these slide tongues cannot be done without tools, or is possible only after detachment of a securing element or after uncovering an access opening into the interior of the housing body. As a result, protection against unintended shifting of the sliding position of the second and third slide tongues can be attained.

In this respect it also proves advantageous if the second slide tongue or the third slide tongue and preferably both of these slide tongues are located displaceably inside the housing body, and thus do not protrude past a side edge of the housing body. By this means as well, effective position against unintended shifting can be achieved.

In a further concept of the invention it is proposed that the second slide tongue or the third slide tongue, and preferably both slide tongues, are nondisplaceably positionable in a given positioning relative to the housing body. This can already be achieved by providing that the slide tongues are received between flat materials in the interior of the housing body, and thus are not accessible from outside, or not without requiring further provisions to be made.

In a further concept of the invention of particular significance, it is proposed that the second slide tongue and/or the third slide tongue has a row of perforations or a row of tool engagement sites, and the spacing of the perforations matches the spacing of the middle of the window or scales of the first, second or third slide tongue in the displacement direction. Providing a row of tool engagement points, in particular a row of perforations, offers the possibility that with a tool, in particular in the form of a stylus or the like, or even merely a fingernail, an intended change in the sliding position of the second or third slide tongue can be performed. It also proves especially advantageous if the device has a portion of flat material as a cover layer on the back side or as a cover layer on the viewing side, in which layer at least one window for access to at least one slide tongue, located in the interior of the housing body, is provided. For instance, through the window or windows, access to the aforementioned row of perforations or row of tool engagement points can then be gained. It also proves advantageous if the window or windows are closeable by a means for preventing access to the second and/or the third slide tongue. This means can for instance be adhesive labels adapted to the window size, or for a particular portion of flat material some other means may be provided, such as a flap or a window release slide, or the like.

In a further advantageous concept of the invention, it is proposed that the first slide tongue prevents access to the second and/or third slide tongue for displacement of the second and/or third slide tongue and only in a certain sliding position of the first slide tongue permits or enables access to the second and/or third slide tongue. This can be attained for instance in that the first slide tongue is located between the second or third slide tongue and a cover layer, which has a window for access, and the first slide tongue has an access window, which, solely in a certain sliding position of the first slide tongue, is aligned relative to the housing body with the window in the cover layer. By this means as well, very effective protection against unintended shifting of the second or third slide tongue can be attained.

In a further concept of the invention, it is proposed that on the second and/or on the third slide tongue, the parameter values are provided successively visually perceptibly in the displacement direction, and thus in particular are printed on, and that in a given sliding position of the second or third slide tongue, a parameter is visually perceptible. This can be attained for instance in that a window is provided in a cover layer, the window being located such that the applicable parameter value in the displaced position of the second or third slide tongue at the time can be visually perceived through this window. In this way, the correct sliding position for the second or third slide tongue, namely in accordance with the particular parameter value to be made the basis at the time, can be found quickly.

It further proves advantageous if a portion of flat material is provided as a cover layer, in which windows for visual inspection of scales, located beneath them, of the slide tongues are provided. These windows may in particular also be embodied as transparent areas of the portion of flat material.

It further proves advantageous if the second and third slide tongue is provided above the first slide tongue, that is, on the viewing side of the device facing toward the user, where the setting and readout are done.

As mentioned, the slide device of the invention is formed of portions of flat material located in layers. Fixedly joined portions of flat material are provided, along with displaceable portions of flat material in the form of the slide tongues. It proves advantageous if the slide tongues are bounded in their displacement direction on both sides and linearly guided by fixed portions of flat material. In this way, the components of the device that form the housing can take on guidance and limitation functions at the same time.

In the second variant of the invention, instead of displaceable slide tongues, portions of flat material in the form of dials are used. A first dial has a plurality of input scales and one output scale. The plurality of input scales are located in succession in the radial direction and each extends in the circumferential direction, or in other words concentrically to the axis of rotation.

A second dial includes a plurality of windows, which are located at various radial spacings and extend in the circumferential direction, that is, concentrically, and are preferably offset from one another in the circumferential direction. By rotation of the second dial relative to the first dial, a specific input scale can thus be put in the vicinity of the viewing window of the second dial. Furthermore, a third dial is provided, with a plurality of reading scales located concentrically and in succession in the circumferential direction, which by rotation can put a specific reading scale of the third dial in the readout position for the output scale on the first dial. The order of the location of the second dial and the third dial can also be reversed and is purely an example here. As in the slide device, in the specific spacings of the scale lines of the various scales, the algorithm that is made the basis and the patient-specific and time-of-day-specific parameter that is made the basis are stored in memory. For the use of the dial device, the second dial and the third dial are rotated into a relative position to one another that corresponds to the parameters to be made the basis and are preferably fixed against one another in this position, which will be described in detail hereinafter. A rotary positioning of the second and the third dial relative to the input scale of the first dial selected by means of the second dial is then performed, so that the amount of bread units or carbohydrate exchange units to be eaten is adjusted via the setting mark at the window of the second dial. As in the slide device, the amount of insulin to be injected can be read off directly at the measured current blood sugar value of the reading scale a,s a reading mark on the output scale.

The advantages of the dial device of the invention are equivalent to the advantages explained above in connection with the slide device of the invention. However, its manipulation might be even simpler and more user-friendly, which should also increase its acceptance by the user.

In a further embodiment according to the invention of the dial device, it proves advantageous if a fourth dial is provided as a cover disk, which has a window that extends radially and in the circumferential direction and that in a selectable rotary position enables an inspection of the reading scale of the third dial and of the output scale of the first dial and, through a window in the second dial, of the input scale of the first dial. In this way, the user can specifically view the user-relevant scales selected in accordance with the positioning of the second and third dials to one another. It also proves to be advantageous if the second and the third dial and optionally the fourth dial can be positioned nonrotatably in a selected rotary position relative to one another. In this way, the patient-specific and time-of-day specific parameters prescribed by the physician or therapist can be set and fixed for further use.

There are many possibilities for making make the second and third dials nonrotatable; these ways differ in manipulation, technical feasibility, and user-acceptance. For instance, it is proposed that for positioning the second and third dials and optionally the fourth dial nonrotatably, an adhesive connection, which in particular can be undone, or a mechanical element for coupling the dials by clamping or in form-locking fashion to one another is provided, in particular in the form of a rivet connection or screw connection.

Since coupling elements between the second and the third dial protrude axially, it proves advantageous that a spacer disk is provided between the first and second dials and that the adhesive connection, which in particular can be undone, or a mechanical element coupling the disks to one another in clamping or form-locking fashion, in particular in the form of a rivet connection or screw connection or seal, is provided radially outside the spacer disk. In this way, a troublesome roughness can be avoided; and in particular, abrasion or other problems in using the dial device are avoided, or at least reduced.

If a mechanical element is used for connecting the dials, it can prove advantageous if the mechanical element coupling the second, third and fourth dials in form-locking fashion to one another is a seal comprising two plastic injection-molded parts, which mesh with one another and reach through stamped perforations in the second, third and fourth dials, and the seal has a rated breaking point, at which, upon an intended resetting of the three dials can be broken off and replaced with a new seal.

It also proves advantageous in terms of the manipulability of the device if the first dial protrudes radially past the other dials and there forms a holding zone for grasping and holding the device while it is being used. When adjusting the second and third disk relative to one another and making them nonrotatable in a selected position, this embodiment of the first dial with a holding zone can prove especially advantageous.

It also proves advantageous if the parameter values are provided successively in the circumferential direction visually perceptibly and, in a selected rotary position of the second and third dials relative to one another, the first and second parameter values are visually perceptible on the viewing side of the device.

If for positioning the second, third and fourth dials nonrotatably, an adhesive connection is used, it proves especially advantageous if an adhesive label is provided, which can be applied to the viewing side of the fourth dial and, through a recess in the fourth dial, can be made to adhere to the third dial and, through a recess in the third dial, can be made to adhere to the second dial, so that the second, third and fourth dials are positioned nonrotatably relative to one another. In this embodiment, the assumption is that the first through fourth dials are arranged in succession in this order: 1-2-3-4.

If the order of the second and third dials is reversed, that is, is 1-3-2-4, then it proves advantageous if for positioning the second, third and fourth dials nonrotatably, an adhesive label is provided, which can be applied to the viewing side of the fourth dial and, through a recess in the fourth dial, can be made to adhere to the second dial and, through a recess in the second dial, can be made to adhere to the third dial, so that the second, third and fourth dials are positioned nonrotatably relative to one another.

In both embodiments, in any case, a recess is provided in the fourth dial, that is, the cover disk, and in the dial adjoining it, that is, in the third or second dial, and all three dials are fixed to one another and against one another by the adhesive label to be applied to the cover disk two-dimensionally at the top and are thus made nonrotatable. It proves especially advantageous if this adhesive label functions at the same time as an information carrier and if the treating physician or therapist can, from the label, document the setting of the parameter values by the fixation of the three disks relative to one another.

It also proves advantageous if the adhesive label is embodied such that it cannot be removed without being destroyed. For that purpose, the adhesive label may have rated breaking lines, so that when it is pulled off, part of it remains on the dial device so that it is self-destructing.

It proves in particular to be advantageous if the recess in the second or third dial is embodied in the form of an oblong slot or kidney or in the form of a row of circumferentially or rotationally successively arranged recesses, and the size of the recess or recesses in the second or third dial is smaller than the size of the recess in the fourth dial, so that the adhesive label can be made to adhere to a surrounding region of the recess or recesses in the second or third dial. In this way it can be ensured that by simple two-dimensional application of an adhesive label to the fourth dial, all three disks are fixed to one another and as a result are made nonrotatable.

The plurality of input scales of the slide device or dial device, although they do each preferably have an equidistant line graduation, nevertheless differ in the spacings of the particular line graduations from one another. On the input scale, the ratio of the spacings of the line graduation of the various input scales to one another is equivalent to the ratio of the first parameter assigned to a given input scale. Since a division is performed for the reading scale, the ratio of the spacings of the line graduation of the various reading scales relative to one another is the inverse ratio of the second parameter assigned to a given reading scale.

As mentioned at the outset, it would be appropriate for the diabetes patient to have a preset slide device or dial device for every time of day. In the case of the dial device, it would also be conceivable that the first dial is reserved as a basic disk and that combinations, preset for each time of day, of the other dials are then rotatably secured to it. For that purpose, the rotary connection at the axis of rotation can be embodied such that it can be, for instance by means of a push button connection that can be easily locked into place and released.

The aforementioned invention also includes slide devices and dial devices which can be used for other purposes than for ascertaining an amount of insulin to be injected. In such other purposes, other algorithms could also be embodied or implemented by means of a specific design of the various scales and their line graduations.

Further features, details and advantages of the invention will become apparent from the appended claims, the drawings, and the ensuing description of preferred embodiments of the invention.

Figure 4:
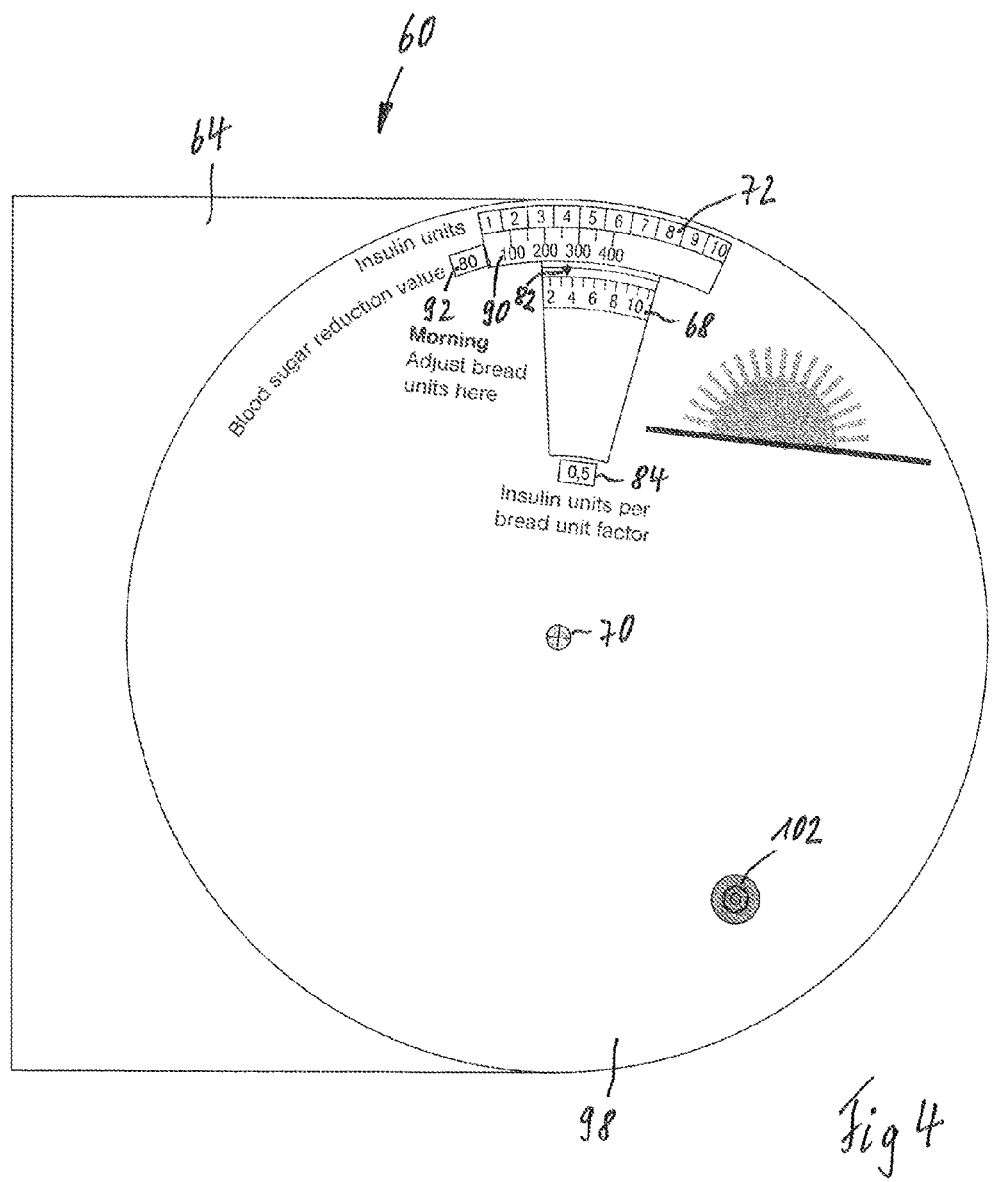

In the drawing:

FIGS. 1*a-d* show four planes of a slide device of the invention;

FIG. 2 is a top view on the slide device;

FIGS. 3*a-e* show various planes of a dial device of the invention;

FIG. 4 is a top view on the dial device; and

Figure 5A:
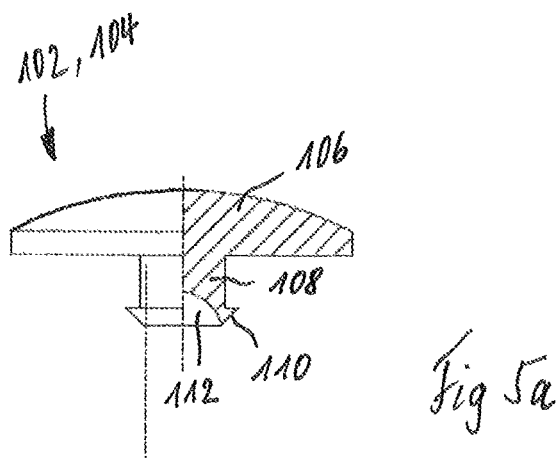

FIGS. 5*a, b* each show one exemplary embodiment for an element for fixation of the rotary position of dials to one another;

FIGS. 6*a-e* show a further embodiment of the dial device of the invention, in which three dials can be placed unshiftably to one another by means of an adhesive label.

FIG. 7 is a table.

First, a typically made calculation of the amount of insulin to be injected on the basis of exemplary bread units or carbohydrate exchange units and exemplary parameters for the insulin factor and the blood sugar reduction value and on the basis of an exemplary blood sugar value measured will be explained with reference to the table in FIG. 7.

Table: calculation of the amount of insulin per FIG. 7:

In lines 1 through 3 of the table, a total of 3.5 bread units or carbohydrate exchange units that are to be eaten at the upcoming mealtimes are made the basis. In line 5, patient-specific insulin factors that are made the basis for various times of day, namely morning, midday, evening and late evening, are shown; as an example for midday, the parameter 0.5 is selected in line 7. From this parameter as an insulin factor, multiplied by the 3.5 bread units or carbohydrate exchange units, the calculation is 1.75 insulin units (line 7). In line 8, a currently measured blood sugar value of 120 is made the basis. In line 10, the time-of-day-specific blood sugar target values are entered for the times of day. In line 12, the deviation of the current blood sugar value of 120 from the blood sugar target value made the basis for midday, which is 100, is shown, namely a difference of 20. In line 14, the patient-specific and time-of day-specific blood sugar reduction values are entered. In line 16, the differential value of 20 from line 12 is divided by the time-of-day-specific blood sugar reduction value for midday of 80, resulting in 0.25 insulin units. In line 17, the insulin units of 1.75 ascertained in line 7 are added to the insulin correction amount from line 16, resulting in 2.0. This is the value that the patient must inject in conjunction with the upcoming midday meal and the snack later.

FIGS. 1a through d show four planes of a slide device 1 of the invention (shown taken apart), specifically from bottom to top, that is, in the direction of the visible side, facing toward the user in operation, of the slide device. In each case, these planes are shown as viewed by the user, that is, toward the side of the applicable plane that faces toward the user. FIG. 1a shows a cover layer 2 on the back, with windows 4 and 6 to be explained hereinafter, in the form of continuous recesses. FIG. 1b shows a second plane in the form of a first slide tongue 8 and two fixed, elongated portions of flat material 10 and 12, each peripherally at bottom and top, which for the intended use are glued unremovably to the cover layer 2 on the back. They form a linear guide for the slide tongue 8 that is displaceable back and forth in the direction of the double arrow 14. The first slide tongue has five input scales 16 and one output scale 18; the scales extend in the displacement direction 14 and are located side by side transversely to the displacement direction 14. In the first slide tongue 8, there are also two windows 20 and 22, to be explained hereinafter, in the form of access recesses.

FIG. 1c shows a third plane. Striplike portions of flat material 24, 26 extending transversely to the displacement direction 14 can be seen, which on their upper and lower ends are each unremovably joined to the striplike portions of flat material 10 and 12 of the second plane, in particular being glued to them. A projecting portion of flat material 28 can also be seen, which is likewise unremovably joined to the striplike portions of flat material 10, 12 at the top and bottom. Between the striplike portions of flat material 24 and 26, a second slide tongue 30 is provided, which is displaceable orthogonally to the displacement direction 14 of the first slide tongue in a direction 32. It has a window 34 with an setting mark 35, which is embodied as an access recess or as a visually transparent area. By displacing the second slide tongue 30 in its displacement direction 32, the window 34 can be positioned in the direction 32 opposite the first slide tongue, located beneath it, at various positions, so that selectively, one of the input scales 16 can be visually perceived through the window 34. For adjusting the second slide tongue 30, a perforation grid 36 extending in the displacement direction 32 is provided, the use of which will be described directly hereinafter.

Between the striplike portion of flat material 26 and the projecting portion of flat material 28, a third slide tongue 38 is provided, which is likewise displaceable in the displacement direction 32, that is, orthogonally to the displacement direction 14 of the first slide tongue 8. The third slide tongue 38 includes a plurality of windows 40, which again are embodied in the form of either continuous recesses or transparent areas. Along each window 40, there is a reading scale 42, whose line graduation extends along the respective longitudinal extent of the window 40, or in other words in the displacement direction 14 of the first slide tongue 8. The third slide tongue 38, too, includes a perforation grid 44, which extends in the displacement direction 32 of the third slide tongue 38.

FIG. 1d shows a cover layer 46, forming the viewing side, in which windows 48 and 50 as a continuous recess or as a visually transparent area permit a visual inspection of the aforementioned scales of the slide tongues located beneath them. Through these same windows 48 and 52, or through further windows 48a and 50a, in the cover layer 46, first parameters 37 (FIG. 1c) and second parameters 45 (FIG. 1c) of the second slide tongue 30 and the third slide tongue 38, respectively, are visually perceptible to the user. The display of these first and second parameters enables the user to make a positioning or sliding position, corresponding to the parameter, of the second slide tongue 30 and the third slide tongue 38.

The aforementioned adjusting of the second slide tongue 30 and the third slide tongue 38, in the embodiment described here as an example, takes place as follows: The user pulls the first slide tongue 8 in the direction of the arrow 14 out of the housing body 52, formed by the fixed layers, as far as the arrow markings 54 (FIG. 1b). In this position, the windows 20 and 22 in the first slide tongue 8 are aligned with the windows 4 and 6 in the cover layer 4 on the back and thus enable access to the perforation grid 36 of the second slide tongue 30 and to the perforation grid 44 of the third slide tongue 38. The user can then, using a styluslike, intrinsically arbitrary, means, reach through the oblong-slot-like windows 4, 6 in the cover layer on the back and through the windows 20, 22 into the respective perforation grid 36, 44 and in this way displace the second and third slide tongues 30 and 38 incrementally by a predetermined position in the direction 32. In doing so, the user observes the housing body 52 of the slide device from behind. Since the second and third slide tongues 30, 38 on the back side likewise have the first parameters 37 and the second parameters 45 in a visually perceptible way, these parameters are each visible through the rectangular windows 4, 6 in the cover lay 2 on the back. Thus the user is given information of the parameters that have been set by displacement of the respective slide tongue 30, 38. After these parameters have been set, that is, once the intended displacement position of the second slide tongue 30 and the third slide tongue 38 have been set, the first slide tongue 8 is pushed back in again. Thus the windows 20, 22 in the first slide tongue 8 move out of the range of overlap of the windows 4 and 6 in the cover layer on the back. Access to the second and third slide tongues 30, 38 is now no longer possible. In this way, the second and third slide tongues 30, 38 are positioned non-displaceably, which effectively prevents an unintentional shifting of the slide tongues 30, 38.

In an alternative embodiment, not shown, it would be conceivable that access to the second and third slide tongues, in particular to the perforation grids 36, 44 of the second and third slide tongues 30, 38, takes place via the cover layer 46 on the viewing side, in that there, in particular at a suitable point of the perforation grids, windows that are preferably elongated and preferably only a few millimeters wide are provided in the form of access recesses.

In both embodiments, it would be possible for the windows in the cover layer to be closable by suitable means to prevent access. In the simplest case, an adhesive label or the like could be provided there.

For the implementation of the slide device of the invention for ascertaining an amount of insulin to be injected, the input scales 16 are embodied in accordance with the first parameter 37 (insulin factor); that is, in the present embodiment, the ratio of the line graduation of the input scales to one another is equivalent to the ratio of the first parameters 37 assigned to a given input scale. By setting the sliding position of the second slide tongue, the input scale 16 corresponding to the corresponding first parameter 37 is brought into the viewing area of the window 34 in the second slide tongue 30. In the exemplary embodiment selected here, the spacings of the line graduation of the respective reading scales from one another correspond to the inverse ratio of the second parameters 45 assigned to a given reading scale 42. In accordance with the sliding position of the third slide tongue 38, the window 40 of the third slide tongue 38 corresponding to the intended second parameter 45 is put into coincidence or overlap with the output scale 18 on the first slide tongue 8. For ascertaining the amount of insulin to be injected, all that has to be done now is for the first slide tongue 8 to be pulled out far enough that the setting mark 35 in the vicinity of the window 34 of the second slide tongue 30 is positioned on the bread units or carbohydrate exchange units to be made the basis. The amount of insulin to be injected can now, at the position of a currently measured blood sugar value as a reading mark on the reading scale 42 be read off on the output scale 18, positioned beneath it, of the first slide tongue 8.

FIG. 2 shows as an example an operating position of the slide device of the invention. The second slide tongue 30 is, with its window 34, in a sliding position corresponding to the insulin factor of 0.5 as a first parameter. The third slide tongue 38 is in a sliding position corresponding to the blood sugar reduction value of 90 as a second parameter. The first slide tongue 8 is pulled out far enough that the setting mark 35 is set for the bread units or carbohydrate exchange units. If a currently ascertained blood sugar value of the patient is now 200, then the amount of insulin to be injected can be read off on the reading scale 42 directly under the value "200", as a reading mark on the output scale 18 of the first slide tongue 8. In the present case, the result is a value between 6.5 and 7, or in other words approximately 6.75 insulin units.

FIGS. 3a through 3e in various planes show a dial device 60 of the invention, again in the order from bottom to top, or in other words in the direction toward the user.

FIG. 3a shows a top view on a portion of flat material which forms a cover layer 62 on the back of the dial device 60. This cover layer on the back at the same time forms a first dial 64. However, it is not embodied as a circular disk but instead includes a rectangular portion 66, which for example protrudes laterally past the projection of a circular disk, by which portion the dial device 60 can be grasped easily in use. The first dial 64 further includes a plurality of input scales 68, which are located or extend at various radial spacings and each concentrically to an axis of rotation 70. Each input scale 68 is assigned a first parameter, namely the so-called insulin factor. This means that in the case shown as an example, the ratio of the spacings of the line graduation of the respective input scale 68 is equivalent to the ratio of the first parameters assigned to a given input scale. Furthermore, on the first dial 64, as an example radially on the outside, a output scale 72 is also provided, extending concentrically.

Figure 3B:
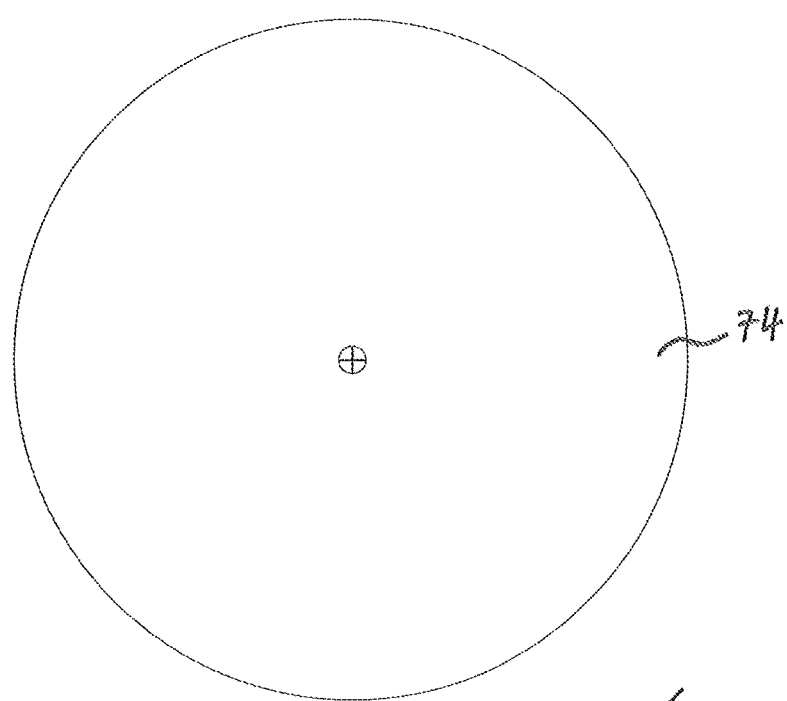

FIG. 3b shows the top view on an optional spacer disk 74, the radius of which is smaller than the spacing of an access recess 76, to be explained hereinafter, in the axis of rotation 70. This access recess 76 is provided at least in the dials to be described hereinafter and optionally in the first dial 64 as well.

Figure 3C:
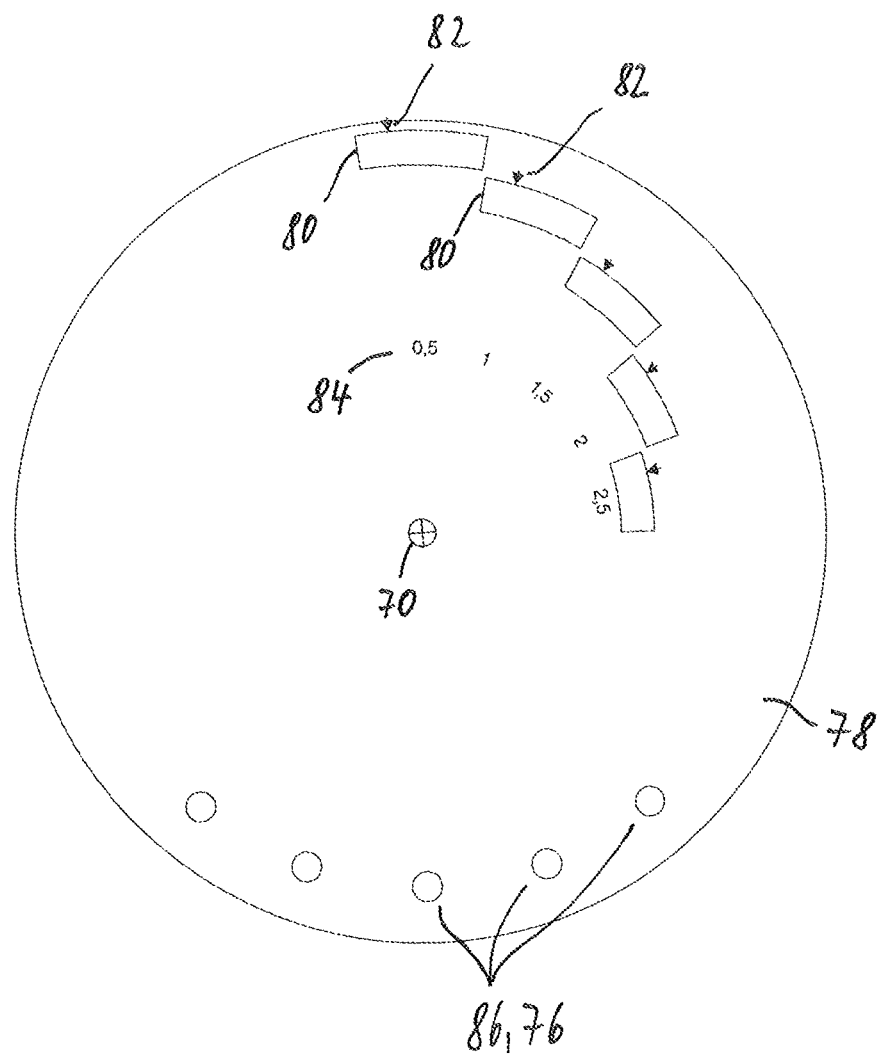

FIG. 3c shows a third plane of the dial device 60 of the invention. It includes a second dial 78 with a plurality of windows 80, which are provided at various radial spacings from the axis of rotation 70. Depending on the rotary position of the second dial 78 relative to the first dial 64, one of the input scales 68 of the first dial 64 can be made to overlap, relative to a "12 o'clock position" of the first dial, with one of the windows 80 in the second dial 78. Also, a setting mark 82 is provided on each window 80; its purpose is that it is positioned opposite a value of the input scale 68.

Radially inside the respective window 80 and concentrically, the first parameter 84, the aforementioned insulin factor, belonging to a given window 80 or to a given input scale 68, is provided in a visually perceptible manner. Further, the second dial 78 has a concentric perforation grid 86, which is formed by the access recesses 76 already mentioned.

FIG. 3d shows a top view on a third dial 88 having a plurality of concentric reading scales 90, which for example are located radially on the outside. The line graduation of these reading scales 90, in the case shown as an example, are in a reciprocal proportion to a second parameter 92 assigned to a given reading scale 90, that is, the blood sugar reduction value, which is likewise provided in a visually perceptible manner next to the applicable reading scale 90. The reciprocal proportion is the result of an algorithm that describes a division. The third dial 88 is embodied in transparent form, radially inside the reading scales 90. It too has a perforation grid 94 of access recesses 76, which is embodied at the same radial spacing from the axis of rotation 70 and at the same angular spacing as the perforation grid 86 in the second dial 78. The order of the arrangement of the second dial 78 and the third dial 88 may also be reversed and is purely exemplary here.

Figure 3E:
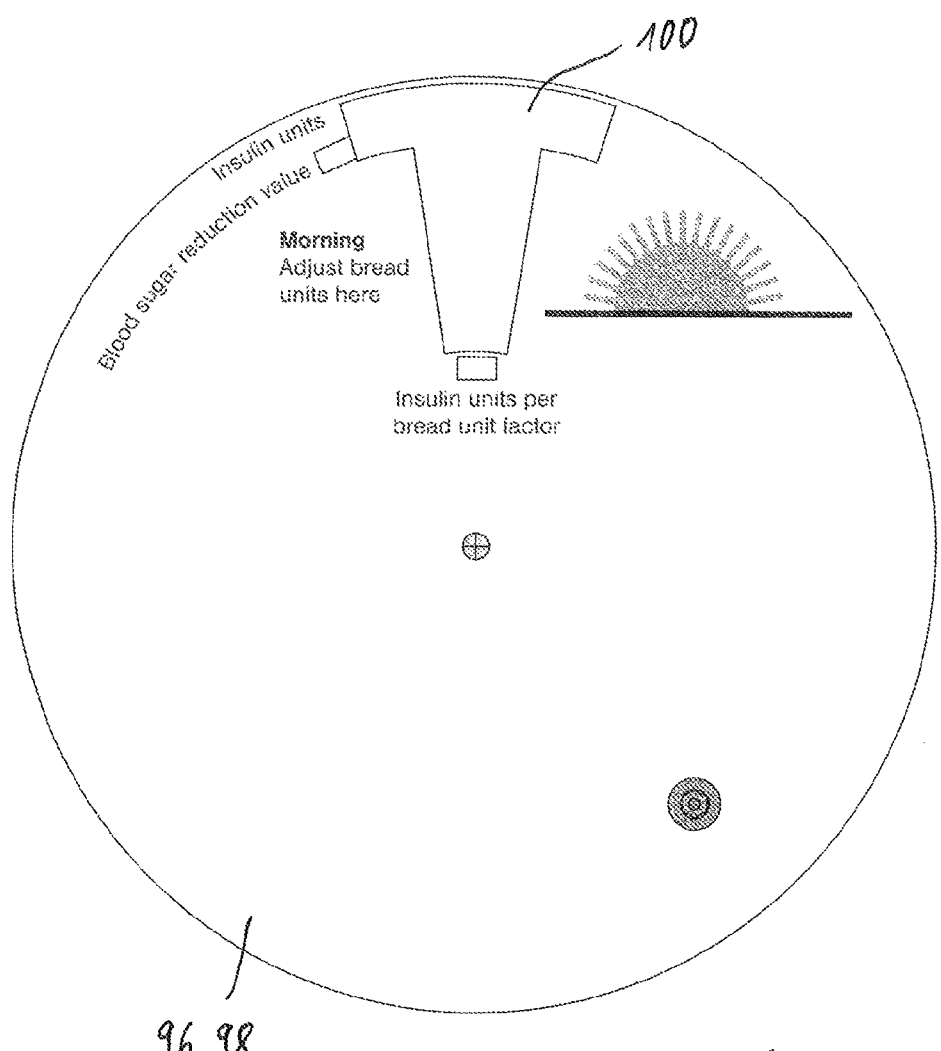

Finally, FIG. 3e shows a portion of flat material which for example is in the form of a circular disk, which forms a cover layer 96 on the viewing side, facing toward the observer, and thus forms a fourth dial 98. The fourth dial 98 includes a radially and circumferentially extending window 100, dimensioned such that in a selectable rotary position, it makes it possible to inspect the scales or scale areas of the other dials that are visible in this rotary position. The window 10 may be formed as a continuous recess or as a transparent area of the fourth dial 98.

In FIG. 4, a top view on the dial device 60 of the invention is shown, based on the parameters of the table explained above. The input scale 68 corresponding to the first parameter 84 (insulin factor) of 0.5 is selected. Furthermore, the reading scale 90, associated with the second parameter 92 (blood sugar reduction value) of 80, is made the basis. If the second dial 78, the third dial 88 and the fourth dial 98 are now fixed in the rotary position thus oriented relative to one another, which can be done for example by means of a splint-like, screw-like or rivet-like element 102, which in the applicable rotated position can be done by means of the access recesses 76, axially aligned with one another, of the respective perforation grid 86, 94, then the thus-fixed combination can be rotated relative to the first dial 64. To ascertain an amount of insulin to be injected, such a rotation of this combination is now made relative to the first dial 64 in such a way that the setting mark 82 is positioned at the applicable window 80 of the second dial 78 opposite the bread units or carbohydrate exchange units to be eaten; in the present case, this is accordingly 3.5 bread units or carbohydrate exchange units. If now as in the example of the table a current blood sugar value of 120 is measured, then the amount of insulin to be injected merely needs to be read off at this value 120 of the reading scale 90 as a reading mark radially outside on the output scale 72. In this case, it is located precisely at two insulin units.

With the slide device 1 of the invention and the dial device 60 of the invention, thus with the first and second parameters set beforehand, a multiplication and division and addition of correspondingly specified algorithms is performed by a single slide or rotary positioning motion. Because in the dial device 60 as well the second, third and preferably also the fourth dials 78, 88, 98 can be positioned nonrotatably relative to one another, in fact by intrinsically arbitrary means, a high degree of operating safety is achieved. Here as well, in addition to the overlapping of the splint-like, screw-like or rivet-like element 102, adhesive labels or the like may be used.

Figure 5B:
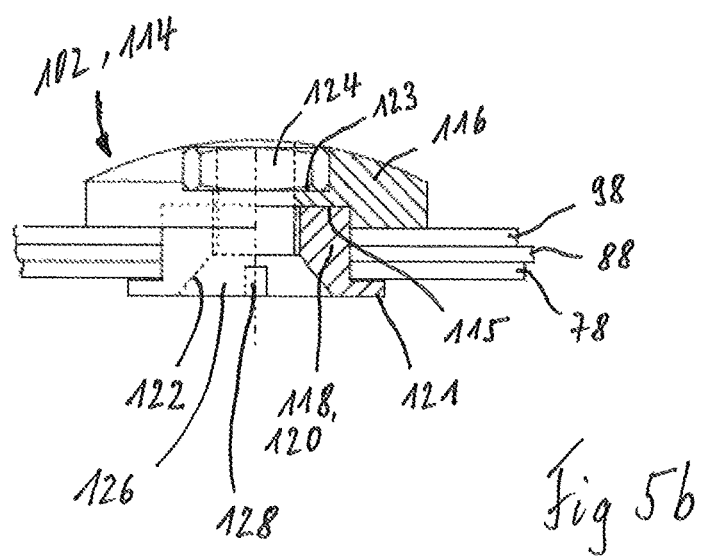

FIGS. 5a and 5b show two exemplary embodiment s for such elements that can in principle be considered. FIG. 5a shows a locking button 104 with a flattened head 106 that tapers radially outward and with a pin or stem 108 protruding in the axial direction. On the axial free end of the pin or stem 108, a radial expansion 110 forming a barb is embodied, which however tapers conically again in the insertion direction. In this way, the locking button 104 can be pushed through the second, third and fourth dials 78, 88, 98; the dimensions of the access recesses 76 and of the pin or stem 108, including its radial expansion 110, is such that when the button is pushed, the radial expansion 110 with its conical embodiment strikes the access recesses 76 and is compressed radially inward elastically and then snaps radially outward back again and thus locks in form-locking and barb-like fashion. This is favored by an axial recess 112 indicated in FIG. 5a. In this exemplary embodiment of the element 102, a high degree of safety against unintended or unknowing changing of the intended rotary position of the disks relative to one another is achieved.

FIG. 5b shows a further embodiment of an element 102 in the form of a multi-part locking button 114. It in turn includes a flattened head 116 and a pin or stem 118, but in the form of a cylindrical sheath 120, which is detachable from the head 116 and has a flange 121 and a conical inner countersunk feature 122 and which is inserted into an axial opening 123 on the head 116. Also, screw means 124 and 126 that can be screwed counter to one another from both sides are inserted; the screw means 124 is inserted into an offset bore in the head 116, and the screw means 126 is inserted into the cylindrical sheath 120. This screw means 126 advantageously has an axial tool engagement point 128. This tool engagement point 128 is accessible for instance through the optional access recess 76 in the first dial 64, in order to unscrew or establish the screw connection, if a change in the rotary position of the dials 78, 88, 98 is to be brought about intentionally. This access recess 76 can if desired be covered and thus secured by means of a label that cannot be detached without being destroyed.

Figure 6A:
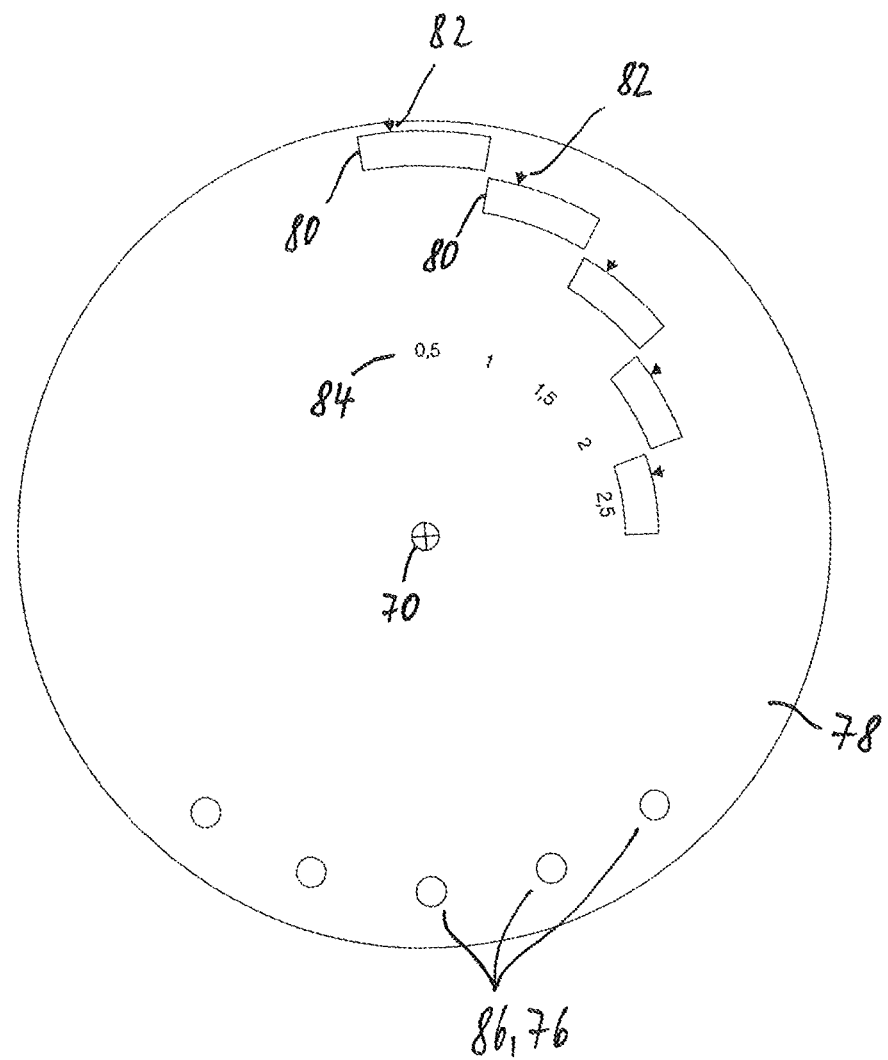
Figure 6C:
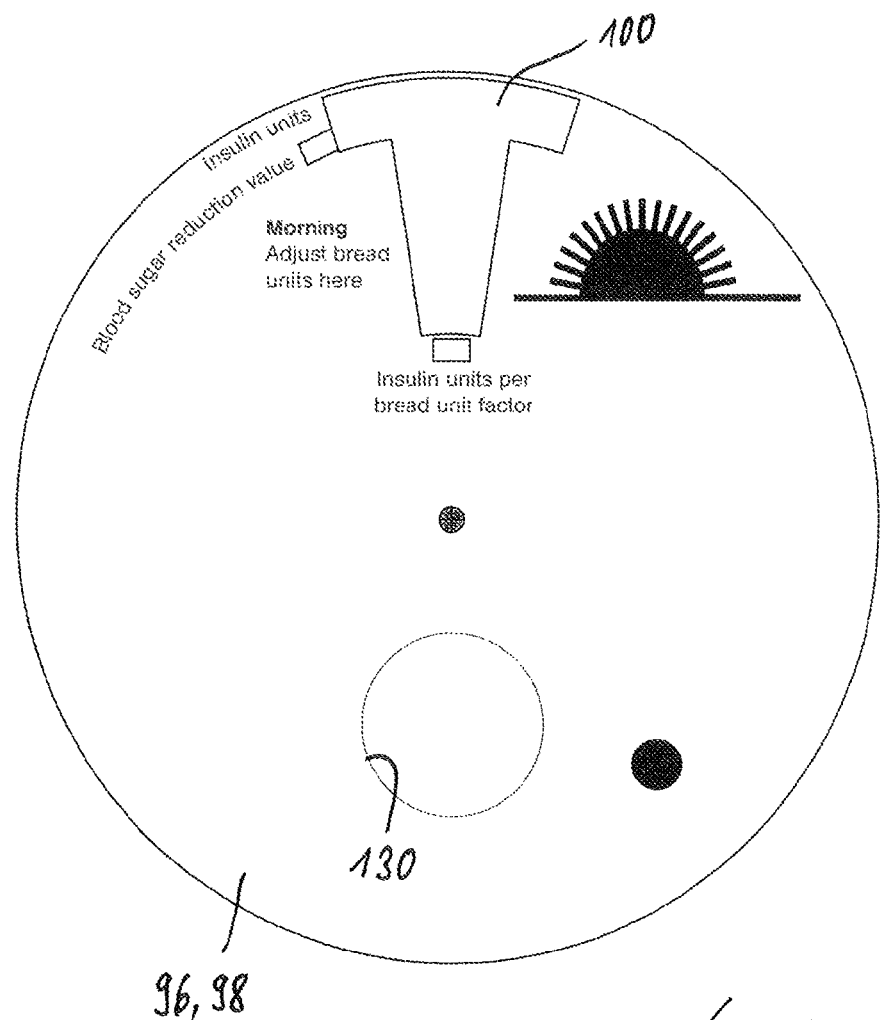
Figure 6D:
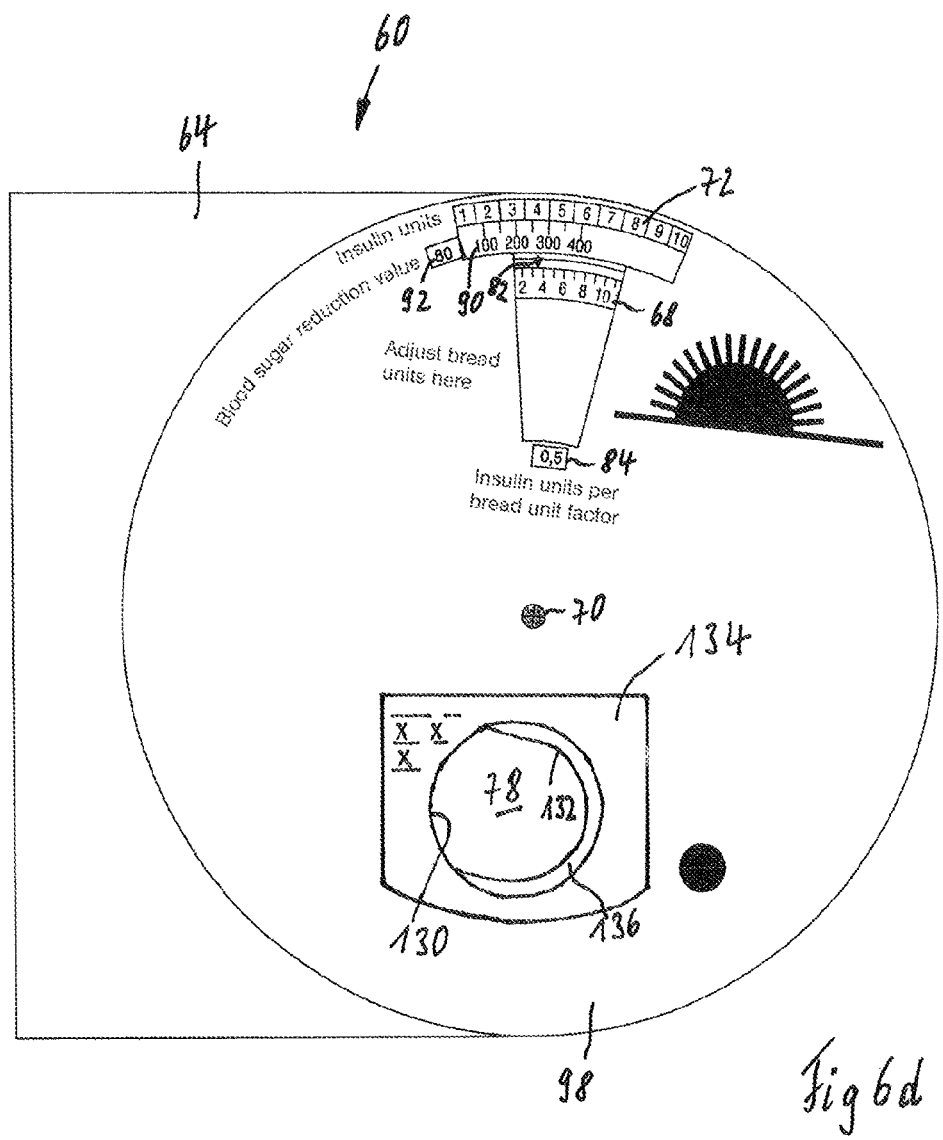
Figure 6E:
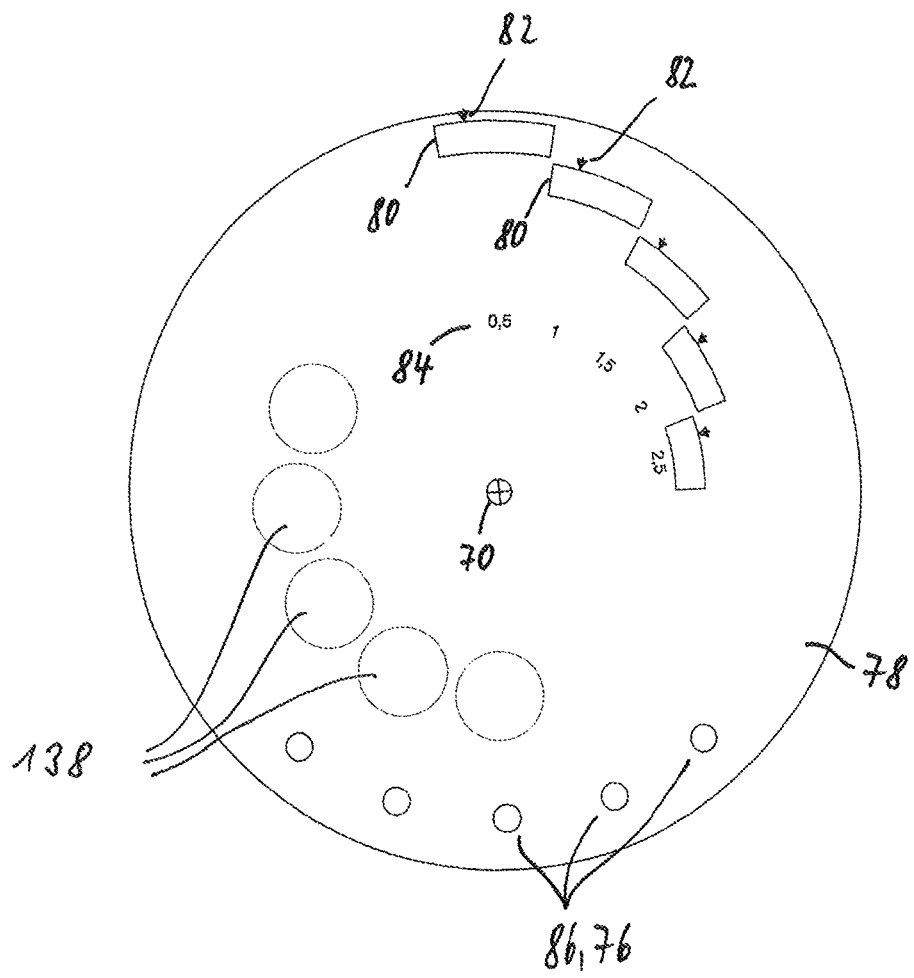

FIGS. 6a-d show a further preferred possibility for making the second, third and fourth dials 78, 88, 98 nonrotatable. FIGS. 6a-c show a top view on these dials 78, 88, 98. In the fourth dial, forming the cover side, a recess 130 can be seen, which for instance is circular, as can an elongated, for instance kidney-shaped or oblong-slot-like recess 132 in the third dial 88 located underneath the recess 130, which are located such that they overlap one another at an appropriate rotary position. This is indicated in FIG. 6d. The size of the recess 132 in the third dial 88 is less in at least one direction than the size of the recess 130 in the fourth dial 98. Through the recess 132 in the third dial 88, a surface region of the second dial 78 is exposed. If the order of location of the second dial 78 and the third dial 88 were reversed, the oblong-slot-like recess 132 would be embodied in the second dial 88. As FIG. 6d shows, the three dials 78, 88 and 98 can be fixed to one another by applying a single adhesive label 134; that is, they can be made nonrotatable relative to one another by that means. From FIG. 6d, it can be seen that the adhesive label 134 is or can be adhesively fixed not only on the region surrounding the opening 130 in the fourth dial and on a region 136 that surrounds the recess 132 and is part of the third dial 88 located underneath it, but also on the top of the second dial 78. The adhesive label can be embodied to self-destruct when detached, so that it is thereby ensured that the dial arrangement has been correctly set and fixed by the responsible physician or therapist. The adhesive label can furthermore be used as an information carrier for comments by the treating physician or therapist; in particular, the selected rotary position can be documented on the viewing side. In this embodiment, providing access recesses 76 for a mechanical coupling element is intrinsically unnecessary, or is contemplated merely as an alternative manner of fixation. Finally, FIG. 6e shows a further embodiment having a plurality of recesses 138, instead of the one elongated kidney-shaped recess 132.

The invention claimed is:

1. A dial device for ascertaining an amount of insulin to be injected, comprising portions of flat material arranged in layers which form a disk housing body, having a plurality of disc shape dials, which are rotatable relative to one another about a common axis of rotation that extends orthogonally to the portions of flat material, wherein a first dial has a plurality of input scales, each with equidistant distribution of scale lines, and an output scale, and the plurality of input scales are arranged in various radial spacings, each concentric with the axis of rotation, and each input scale is assigned a first parameter;

wherein a second dial has a plurality of windows, which are embodied in such a way and arranged in various radial spacings, each concentric with the axis of rotation, that a given window, given a suitably selectable rotary position of the second dial relative to the first dial, enables a visual inspection of the input scale, and a given window has a setting mark;

wherein a third dial has a plurality of reading scales, arranged concentrically and in succession in the circumferential direction, each with equidistant scale lines, and each reading scale is assigned a second parameter, and the respective reading scale borders the output scale either radially inward or radially outward;

wherein a fourth dial is provided as a cover disk, which has a window which extends radially and in the circumferential direction and which in a selectable rotary position enables an inspection of the reading scale of the third dial and of the output scale of the first dial and, through a window in the second dial, of the input scale of the first dial;

wherein the second dial and the third dial and the fourth dial can be positioned nonrotatably in a selected rotary position relative to one another; and wherein after the rotary position of the second and third dials has been adjusted relative to one another, in accordance with a value of the first and second parameters, the first dial can be positioned opposite the setting mark at the window of the second dial and then, at a value of the reading scale as a reading mark, a value on the output scale that is equivalent to the amount of insulin to be injected can be read out.

2. The dial device of claim 1, characterized in that for positioning the second, third and fourth dials nonrotatably, an adhesive connection, or a mechanical element for coupling the dials by clamping or in form-locking fashion to one another is provided.

3. The dial device of claim 2, characterized in that the mechanical element coupling the second, third and fourth dials in form-locking fashion to one another is a seal comprising two plastic injection-molded parts, which mesh with one another and reach through stamped perforations in the second, third and fourth dials, and the seal has a rated breaking point, at which, upon an intended resetting of the three dials can be broken off and replaced with a new seal.

4. The dial device of claim 2, wherein a rivet connection, a screw connection or a seal is provided.

5. The dial device of claim 1, characterized in that the first dial protrudes radially past the other dials and there forms a holding zone for grasping and holding the device while it is being used.

6. The dial device of claim 1, characterized in that the parameter values are provided successively in the circumferential direction visually perceptibly and, in a selected rotary position of the second and third dials relative to one another, the first and second parameter values are visually perceptible on the viewing side of the device.

7. The dial device of claim 1, characterized in that for positioning the second, third and fourth dials nonrotatably, an adhesive label is provided, which can be applied to the viewing side of the fourth dial and, through a recess in the fourth dial, can be made to adhere to the third dial and, through a recess in the third dial, can be made to adhere to the second dial, so that the second, third and fourth dials are positioned nonrotatably relative to one another.

8. The dial device of claim 7, characterized in that the recess in the second or third dial is embodied in the form of an oblong slot or kidney or in the form of a row of circumferentially or rotationally successively arranged recesses, and the size of the recess or of the recesses in the second or third dial is smaller than the size of the recess in the fourth dial, so that the adhesive label can be made to adhere to a surrounding region of the recess or of the recesses in the second or third dial.

9. The dial device of claim 7, characterized in that the adhesive label cannot be removed without being destroyed.

10. The dial device of claim 9, wherein the adhesive label has breaking lines.

11. The dial device of claim 1, characterized in that for positioning the second, third and fourth dials nonrotatably, an adhesive label is provided, which can be applied to the viewing side of the fourth dial and, through a recess in the fourth dial, can be made to adhere to the second dial and, through a recess in the second dial, can be made to adhere to the third dial, so that the second, third and fourth dials are positioned nonrotatably relative to one another.

12. The dial device of claim 11, characterized in that the recess in the second or third dial is embodied in the form of an oblong slot or kidney or in the form of a row of circumferentially or rotationally successively arranged recesses, and the size of the recess or of the recesses in the second or third dial is smaller than the size of the recess in the fourth dial, so that the adhesive label can be made to adhere to a surrounding region of the recess or of the recesses in the second or third dial.

13. The dial device of claim 11, characterized in that the adhesive label cannot be removed without being destroyed.

14. The dial device of claim 13, wherein the adhesive label has breaking lines.

* * * * *